United States Patent [19]

Huitson

[11] 4,179,522

[45] Dec. 18, 1979

[54] CERTAIN COMPLEX SALTS OF MONO CARBOXYLIC ACIDS USED AS PRESERVATIVES

[75] Inventor: John J. Huitson, Banstead, England

[73] Assignee: BP Chemicals Limited, London, England

[21] Appl. No.: 735,160

[22] Filed: Oct. 26, 1976

[30] Foreign Application Priority Data

Nov. 27, 1975 [GB] United Kingdom .............. 48779/75

[51] Int. Cl.$^2$ .......................... A01N 9/00; A01N 9/24
[52] U.S. Cl. .................................. 424/317; 424/287; 424/294
[58] Field of Search ................ 424/317, 287, 294, 166

[56] References Cited

U.S. PATENT DOCUMENTS

| | | | |
|---|---|---|---|
| 2,965,488 | 12/1960 | Belasco | ....................................... 99/2 |
| 3,323,987 | 6/1967 | Frensch | ................................ 424/294 |
| 3,786,086 | 1/1974 | Skov et al. | ............................ 260/540 |
| 3,899,588 | 8/1975 | Skov et al. | ............................ 424/317 |

FOREIGN PATENT DOCUMENTS 1451352 9/1976 United Kingdom .
1255205 12/1971 United Kingdom .

OTHER PUBLICATIONS

Chemical Abstracts 64: 4195f (1966).
Chemical Abstracts 60: 12416g (1960) (Thornton).

*Primary Examiner*—Leonard Schenkman
*Attorney, Agent, or Firm*—Brooks, Haidt, Haffner & Delahunty

[57] ABSTRACT

This invention relates to a liquid composition comprising a $C_3$–$C_8$ carboxylic acid, an ion selected from $NH_4^+$ and a Group I or Group II metal according to the Periodic Table due to Mendeleef, and water, the ratio of acid to cation is between 2.1 and 4:1 on a chemical equivalent basis.

9 Claims, No Drawings

CERTAIN COMPLEX SALTS OF MONO CARBOXYLIC ACIDS USED AS PRESERVATIVES

The present invention relates to novel compositions suitable for industrial, agricultural and pharmaceutical applications.

Hitherto saturated and unsaturated aliphatic carboxylic acids, have only been sparingly used in industry and agriculture. The obnoxious odour of the free acids has made the handling of these acids unpleasant for the operatives and their corrosive nature has severly limited their use. It has been suggested, in the past that this disadvantage may be overcome by employing the acids as their neutral salts or their esters. The obvious expedient of using the esters or neutral salts has been unsatisfactory since the acids on esterification or neutralisation lose a considerable amount of their activity.

It has now been found that by adding a base to an acid in aqueous solution in an amount which is less than the chemical equivalent required for full neutralisation, such compositions minimise to a substantial extent the odour and corrosivity of the acids without significant loss of activity of the free acid. In addition, it has surprisingly and unexpectedly been found that the base and acid combine under these conditions to form complexes which are stable in aqueous solutions. Such complexes also have the added advantage that they exhibit neglible vapour loss relative to the free acids and hence retain the preservative activity on the substrate for a longer period of time.

Accordingly, the present invention is a liquid composition comprising ammonium ions and/or ions of a metal selected from Group I and Group II of the Periodic Table due to Mendeleef, a $C_3$-$C_8$ carboxylic acid and water the ratio of acid to ammonium and/or metal ions being in the range of 2:1 and 4:1 on a chemical equivalent basis.

The compositions of the present invention contain one or more carboxylic acids selected from saturated and unsaturated, aliphatic monocarboxylic acids having from 3-8 carbon atoms, preferably containing 3 or 4 carbon atoms. Propionic, n-butyric, isobutyric, n-valeric, 2-methylbutyric, levulinic, acrylic and methacrylic acids are the most preferred.

The Group I and Group II metals of the Periodic Table due to Mendeleef are preferably selected from sodium, potassium, calcium and magnesium. Although metal ions such as copper, strontium and beryllium may also be used, it will be clear that such compositions can only be used for certain special applications e.g. involving pesticidal or fungicidal activity, due to the known toxic nature of the cation. The chemical equivalent ratio of acid to cation is between 2:1 and 4:1. The amount of each component would naturally vary within these ranges depending upon the nature of the cation and the intended use of the composition.

The minimum amount of water in the compositions of the present invention will depend upon the solubility of the complex acid salts contained therein. Thus the calcium and magnesium acid salts would be somewhat less soluble than the sodium and ammonium salts. The concentration of water would therefore be suitably between the minimum necessary to form a homogeneous solution up to a maximum of 90% by weight, preferably between 15 and 75% by weight of the total composition. The weights of the products are calculated as the mass weight of the product applied.

The compositions of the present invention may contain one or more complex acid salts. For example when ammonia is added to aqueous propionic acid the resulting composition may contain ammonium dipropionate as the complex acid salt. Similarly by suitable choice of cations and acid any number of complexes such as ammonium diisobutyrate, sodium dipropionate, calcium tetrapropionate, magnesium tetrapropionate etc. may be present. Although the existence of some similar compounds has been reported in literature, there was hitherto no evidence that these were stable in aqueous solution nor indeed that such compounds exhibit enhance beneficial activity when compared with the free acids. Their existence in solution has now been confirmed by Raman spectroscopy.

The complex acid salt may be prepared by mixing a carboxylic acid with a calculated amount of a base of the desired cation in an aqueous medium. For example, in preparing compositions containing the ammonium ion the acid may be mixed with a concentrated aqueous ammonia solution. On the other hand, for preparing compositions containing the calcium ion, a full calcium salt of the acid may be dissolved in an appropriate amount of the free acid or the free acid may be partially neutralised by lime or reacted with limestone.

The composition may be prepared prior to use or the acid and base components forming the composition may be added separately but simultaneously at the point of application.

The compositions of the present invention with a suitable cation may be used as a preservative for animal feedstuffs and agricultural crops to prevent growth of mould, bacteria and fungi. This may be achieved by applying the composition to the desired substrate as hereinafter defined.

By the term "substrate" is meant here and throughout the specification grass, agricultural crops and/or compounded animal feedstuffs and materials used in preparation thereof such as barley, wheat, oats, rye, maize, rice, hay, straw, silage, dried grass, tick beans, soya beans, bagasse, sunflower seed, sugar cane, rape seed, groundnuts, fish meal, meat and bone meal, buckwheat chaff and wood shavings. Animal excreta may also be treated by the present compositions.

The preservative compositions of the present invention may contain one or more complex acid salts or a mixture of the free acid and the acid salt which may be formed "in situ" during the preparation of the composition. The composition may also contain other conventional additives, in particular those with fungicidal or bacteriocidal properties, such as formalin, formic acid, acetic acid, sorbic acid, dehydroacetic acid and bisulphites.

The amount of composition used for the preservation of a substrate would depend not only on the substrate to be preserved but also on the acidic and cationic ingredients thereof. For example, copper which is nutritionally valuable and is a known growth promoter in animal feed would be used in low concentrations. On the other hand, compositions containing ammonium ions can be used within a wide range of concentrations without any deleterious effect. Thus, the liquid compositions of the present invention when applied as a preservative to a substrate suitably contain between 0.1 and 5% of the inorganic complex acid salts based on the weight of the substrate treated. It is preferably between 0.1 and 2.5% by weight of the substrate treated. The liquid compositions may be applied to the substrates before, during or after harvest or to standing crops.

Other applications of the compositions of the present invention include use in industry for removal of scales from pipes and boilers. In the pharmaceutical industry one of the uses may be in the treatment of fungal infections such as athlete's foot. Such solutions also exhibit buffering activity and may find use in photographic applications. The ammonium and sodium ion containing solutions may be useful as antifreezes. Copper containing solutions may be used for example as wood preservatives and in vine fungicides.

The invention is further illustrated with reference to the following Examples.

EXAMPLES

Examples 1-14

In each example 100 g of barley, which has been remoistened to 30% moisture content (wet mass basis), was treated with the product under test, mixed thoroughly, then stored in a loosely capped bottle in a humidity cabinet maintained at 23° C. and 100% relative humidity. Each treatment was carried out in duplicate or triplicate. The stored grain was examined regularly for the first appearance of mould growth.

The Examples were terminated after one year, at which time many of the samples were still mould-free (the time for mould to appear is shown as >365 days for mould-free samples).

The comparative tests A–G and the control experiments (X) were carried out under the same conditions as above except for using the appropriate free acid or fully neutral salts as indicated in the Tables below.

Examples 15-18

In these examples the compositions as shown in the table were applied during baling of moist hay (31% moisture content), the bales were then stacked and the stacks analysed for mould tests as shown.

The comparative test H and the control experiments ($X^1$) were carried out under the same conditions but without an additive and using the free acids respectively.

Examples 1-14
Barley (30% m.c.) Storage Data with Compositions

| Ex. No. | Composition Applied (Chemical Eqvt. Ratio) Acid | Cation | Method of Application | Complex Identified | Treatment level % m/m of composition applied | Days to Mould | | |
|---|---|---|---|---|---|---|---|---|
| 1. | Propionic Acid 2 | $NH_4^+$ 1 | 80% Aq. Soln. | Ammonium dipropionate | 0.5 | 36 | 36 | 47 |
| 2. | Propionic Acid 2 | $NH_4^+$ 1 | " | Ammonium dipropionate | 0.75 | >365 | >365 | >365 |
| 3. | n-Butyric Acid 2 | $NH_4^+$ 1 | " | Ammonium di-n-butyrate | 0.5 | 29 | 29 | 35 |
| 4. | n-Butyric Acid 2 | $NH_4^+$ 1 | " | Ammonium di-n-butyrate | 0.75 | 99 | 109 | 305 |
| 5. | n-Butyric Acid 2 | $NH_4^+$ 1 | " | Ammonium di-n-butyrate | 1.0 | >365 | >365 | >365 |
| 6. | iso-Butyric Acid 2 | $NH_4^+$ 1 | " | Ammonium di-iso-butyrate | 0.5 | 29 | 29 | 52 |
| 7. | iso-Butyric Acid 2 | $NH_4^+$ 1 | " | Ammonium di-iso-butyrate | 0.75 | 93 | 93 | 109 |
| 8. | iso-Butyric Acid 2 | $NH_4^+$ 1 | " | Ammonium di-iso-butyrate | 1.0 | >365 | >365 | >365 |
| (X) | Propionic Acid | — | " | — | 0.44 | 51 | >365 | — |
| (X) | " | — | " | — | 0.5 | >365 | >365 | — |
| 9. | Propionic Acid 2 | $NH_4^+$ 1 | 70% Aq. Soln. | Ammonium dipropionate | 0.21 | 15 | | |
| 10. | Propionic Acid 2 | $NH_4^+$ 1 | 75% Aq. Soln. | Ammonium dipropionate | 0.23 | 16 | | |
| 11. | Propionic Acid 3 | $NH_4^+$ 1 | 70% Aq. Soln. | Ammonium dipropionate Propionic Acid | 0.21 | 18 | | |
| G | Propionic Acid 1 | $NH_4^+$ 1 | 70% Aq. Soln. | Ammonium propionate | 0.21 | 4 | | |
| 12. | Propionic Acid 2 | $Na^+$ 1 | 70% Aq. Soln. | Sodium dipropionate | 0.21 | 11 | | |
| 13. | Propionic Acid 2 | $Ca^{++}$ 1 | 45% Aq. Soln. | Calcium tetra-propionate | 0.21 | 12 | | |
| 14. | Propionic Acid 2 | $Mg^{++}$ 1 | 25% Aq. Soln. | Magnesium tetra-propionate | 0.21 | 13 | | |
| (X) | Propionic Acid | — | 70% Aq. Soln. | Magnesium tetra-propionate | 0.21 | 27 | | |

G - Comparative Test
(X) - Control Experiment

| | COMPARATIVE TESTS | | | | |
|---|---|---|---|---|---|
| Ex. No. | Composition Applied | Method of Application | Treatment Level % m/m of Composition Applied | Days to Mould | |
| A | Ammonium Propionate | As an 50% Aqueous Solution | 0.75 | 34 | 34 | 34 |
| B | Ammonium Propionate | As an 50% Aqueous Solution | 1.0 | 42 | 45 | 45 |

-continued

COMPARATIVE TESTS

| Ex. No. | Composition Applied | Method of Application | Treatment Level % m/m of Composition Applied | Days to Mould | | |
|---|---|---|---|---|---|---|
| C | Ammonium Butyrate | As an 50% Aqueous Solution | 0.75 | 34 | 34 | 42 |
| D | Ammonium Butyrate | As an 50% Aqueous Solution | 1.0 | 45 | 51 | 51 |
| E | Ammonium Isobutyrate | As an 50% Aqueous Solution | 0.75 | 35 | 37 | 37 |
| F | Ammonium Isobutyrate | As an 50% Aqueous Solution | 1.0 | 100 | 100 | 190 |
| (X) | Propionic Acid | As an 50% Aqueous Solution | 0.35 | 190 | >365 | — |
| (X) | Propionic Acid | As an 50% Aqueous Solution | 0.4 | 92 | >365 | — |
| (X) | Propionic Acid | As an 50% Aqueous Solution | 0.45 | >365 | >365 | — |

A to F - Comparative Tests
(X) - Control Experiment

Examples 15-18
Summary of Compositions used for field trial with Hay

| Ex. No. | Composition Applied (chemical Eqvt. Ratio) Acid | Cation | Method of Application | Complex identified | Treatment level % m/m of Composition Applied | % loss of composition After 31 days | Mold Count (No/g) After 8 days | After 31 days |
|---|---|---|---|---|---|---|---|---|
| H | — | — | — | — | — | — | 21 × 10³ | 53 × 10³ |
| (X¹) | Propionic Acid | — | 70% Aq. Soln. | — | 0.95 | 58.0 | 4.5 × 10⁵ | 65× 10³ |
| (X¹) | " | — | 70% Aq. Soln. | — | 1.35 | 36.0 | <100 | <100 |
| 15. | Propionic Acid 2 | NH₄⁺ 1 | " | Ammonium Dipropionate | 0.98 | 0 | <100 | <100 |
| 16. | Propionic Acid 2 | NH₄⁺ 1 | " | Ammonium Dipropionate | 1.76 | 4.0 | <100 | <100 |
| 17. | Propionic Acid 3 | NH₄⁺ 1 | " | Ammonium Dipropioniate propionic acid | 0.98 | 30.0 | <100 | 5 × 10³ |
| 18. | Propionic Acid 3 | NH₄⁺ 1 | " | Ammonium Dipropionate propionic acid | 1.35 | 21.0 | <100 | <100 |

H - Comparative Test
(X¹) - Control Experiment

The principal advantages of using the compositions of the present invention are that (a) they are less caustic to skin and hence considerably safer to the operative, (b) they are less corrosive to metals than the free acids, (c) they do remove paint and grease and so do not promote deterioration of equipment, (d) they have a lower vapour pressure than the free acids and hence not only reduce environmental hazards due to evaporation but also make more efficient use of the preservative composition applied on the substrate, (e) they do not attack soft seals and pipes and hence facilitate equipment design, (f) they reduce, and in cases eliminate, the obnoxious odour of the preservative acids, (g) they are appreciably more active than the neutral salts and only marginally less active than the free acids, (h) they have a greater solubility in water than the neutral salts and hence facilitate formulation, (i) they can be used as a medium for introducing nutritionally beneficial cations into the substrates preserved.

I claim:

1. A process for preserving substrates against degradation by microorganisms comprising applying to the said substrate a preservative effective amount of a liquid composition comprising in aqueous solution a complex salt of a cation of ammonium, sodium, potassium, calcium or magnesium and at least one monocarboxylic acid selected from the group consisting of propionic acid, isobutyric acid, and butyric acid, the ratio of acid to cation in the complex salt being in the range of 2:1 and 4:1 on a chemical equivalent basis and the concentration of water in the aqueous solution being between 15% and 75% by weight of the total composition.

2. A process according to claim 1 wherein 0.1 to 5% of the liquid composition based on the weight of the substrate is used to treat the substrate.

3. A process as defined in claim 1 wherein said cation is ammonium or sodium and the ratio of acid to cation in the complex salt is in the range of 2:1.

4. A process as defined in claim 3 wherein said cation is ammonium.

5. A process according to claim 3 wherein said cation is sodium.

6. A process as defined in claim 1 wherein said concentration of the complex in the aqueous solution is about 70% by weight of the total composition.

7. A process as defined in claim 4 wherein said concentration of the complex in the aqueous solution is about 70% by weight of the total composition.

8. A process according to claim 1 wherein said cation is ammonium.

9. A process according to claim 1 wherein said cation is sodium.

* * * * *